United States Patent [19]
Krimmer et al.

[11] Patent Number: 5,765,538
[45] Date of Patent: Jun. 16, 1998

[54] PUMP DEVICE FOR A FUEL VAPOR RETENTION SYSTEM OF AN INTERNAL COMBUSTION ENGINE

[75] Inventors: Erwin Krimmer, Pluederhausen; Helmut Denz, Stuttgart; Wolfgang Schulz, Bietigheim-Bissingen; Ernst Wild, Oberriexingen; Winfried Kuhnt, Stuttgart; Helmut Schwegler, Pleidelsheim; Andreas Blumenstock, Ludwigsburg; Tilman Miehle, Kernen; Manfred Zimmermann, Bad Rappenau, all of Germany

[73] Assignee: Robert Bosch GmbH, Stuttgart, Germany

[21] Appl. No.: 793,581
[22] PCT Filed: May 10, 1996
[86] PCT No.: PCT/DE96/00815
  § 371 Date: May 15, 1997
  § 102(e) Date: May 15, 1997
[87] PCT Pub. No.: WO97/02421
  PCT Pub. Date: Jan. 23, 1997

[30] Foreign Application Priority Data
Jun. 30, 1995 [DE] Germany .................. 195 23 935.0

[51] Int. Cl.⁶ ................................................. F02M 37/04
[52] U.S. Cl. ................................. 123/516; 123/519
[58] Field of Search ........................... 123/516, 518, 123/519, 520, 521; 417/413.1

[56] References Cited

U.S. PATENT DOCUMENTS

| | | | |
|---|---|---|---|
| 5,499,614 | 3/1996 | Busato et al. | 123/520 |
| 5,603,359 | 2/1997 | Harris | 123/519 |
| 5,635,630 | 6/1997 | Dawson et al. | 123/520 |
| 5,651,350 | 7/1997 | Blomquist et al. | 123/520 |

*Primary Examiner*—Thomas N. Moulis
*Attorney, Agent, or Firm*—Edwin E. Greigg; Ronald E. Greigg

[57] ABSTRACT

A pump device for performing a leak diagnosis of a fuel vapor retention system. The pump device is provided for a fuel vapor retention system of an internal combustion engine, having a pump membrane driven by an electromagnet and a magnetic armature, which membrane defines a supply chamber that has valve devices, wherein a first valve can be connected to ambient air via a delivery line and can be connected via a second valve to a feed pipe that has an adsorption filter, and having a stop valve between the delivery line and the feed pipe, which valve is embodied so that it can be electromagnetically actuated. The pump device according to the invention is provided for a fuel vapor retention system of an internal combustion engine.

14 Claims, 6 Drawing Sheets

PUMP DEVICE FOR A FUEL VAPOR RETENTION SYSTEM OF AN INTERNAL COMBUSTION ENGINE

PRIOR ART

The invention is based on a pump device for a fuel vapor retention system of an internal combustion engine. A pump device has already been disclosed (WO 94/15090) which is provided for leak testing a fuel vapor retention system in order to deliver a definite volume of air via a ventilation connection of an adsorption filter to a fuel tank of the engine by means of the pump device so that a pressure increase is produced. In order to determine whether the fuel vapor retention system is pressure tight, some time is allowed to pass after the pressure increase finishes in order to indicate a leak when there is a pressure decrease in the fuel vapor retention system, wherein the time elapsed for the pressure decrease is a measure for the size of the leakage opening. Furthermore, the fuel vapor retention system includes a regenerating valve provided between the adsorption filter and an intake pipe of the engine to introduce the fuel vapor temporarily stored in the adsorption filter into the intake pipe by means of the regenerating valve.

The pump device disclosed in the prior art has a pump membrane which is acted upon alternatingly with vacuum and ambient pressure to drive the pump device. When the engine is running, the vacuum is taken from the intake pipe of the engine via a vacuum hose, and via an on-off valve, which is embodied for example in the form of a solenoid valve, is delivered to a pump chamber of the pump device, which chamber is defined by the on-off valve and the pump membrane. By switching the on-off valve, vacuum and ambient pressure are alternatingly set in the pump chamber. When the pump chamber is acted upon with vacuum, the pump membrane moves counter to the compression force of a pump spring, wherein air flows out of a delivery line into a supply chamber disposed opposite the pump chamber, which supply chamber is closed off by the pump membrane and two stop valves, a suction relief valve and a pressure relief valve. With the subsequent impingement of ambient pressure on the pump chamber, the pump membrane moves in the opposite direction, supported by the compression force of the pump spring, wherein the air enclosed in the supply chamber is compressed. When a certain excess pressure is reached in the supply chamber, the pressure relief valve opens so that the ambient air compressed in the supply chamber flows into the ventilation connection of the adsorption filter via the feed pipe in order to produce a pressure increase in the fuel tank.

In the prior art indicated, the switching process by means of the on-off valve is controlled by a so-called reed switch, which is known to one skilled in the art. The reed switch is actuated by magnetic forces and is attached for example to an outer surface of a sleeve in which a pump plunger attached to the pump membrane is guided so that the pump plunger can move longitudinally. A permanent magnet is provided on an end of the sleeve opposite from the reed switch in order to produce a corresponding change of the magnetic field of the permanent magnet on the reed switch depending on the position of the pump plunger in the sleeve so that when the end position of the pump plunger is reached, the reed switch is correspondingly actuated. The position determination of the pump plunger by means of the reed switch, though, is connected with high tolerances and thus does not permit a precise determination of the position of the pump membrane or the position of the pump plunger in the sleeve so that the determination of the size of the leakage opening is only possible in an imprecise manner.

A pump device driven by a vacuum prevailing in the intake pipe is usually provided in the vicinity of the adsorption filter, which is preferably disposed in the region of the fuel tank of a vehicle. The fuel tank is ordinarily accommodated in the rear region of the vehicle, resulting in a relatively long vacuum hose from the pump device on the adsorption filter to the intake pipe of the engine. Since a leak or a tear in the vacuum hose would put the pump device out of commission, a vacuum hose of this kind must be placed in a particularly protected manner on the bottom of the vehicle, though, which creates considerable costs.

The pump device driven by the vacuum of the intake pipe has the disadvantage, moreover, that a leak diagnosis can only be carried out when there is a sufficient vacuum in the intake pipe. The leak diagnosis is therefore essentially limited to the idling range of the engine, which is characterized by a high vacuum. In the upper partial load range or in the full load range as well as when the engine is switched off, there is not sufficient vacuum to drive the pump device so that a leak diagnosis is not possible.

Furthermore, during the leak diagnosis, air is aspirated from the pump chamber into the intake pipe with each switching procedure of the on-off valve, at the transition from ambient pressure to vacuum. This can lead to fluctuations of the air quantity flowing in the intake pipe, though, which is already apportioned by a throttle mechanism disposed in the intake pipe, upstream of the withdrawal point of the vacuum connection so that in particular in the critical region of the idling of the engine, the pulsating introduction of air can produce difficulties in the preparation of a fuel-air ratio to be precisely maintained in the combustion chambers of the engine.

ADVANTAGES OF THE INVENTION

The pump device according to the invention, has the advantage over the prior art that a leak diagnosis can be carried out at any time in a simple manner with the pump device according to the invention, independent of the operational regions of the engine and even when the engine is switched off. The vacuum connection on the pump device that is required in the prior art can be eliminated, by means of which the pump device according to the invention is more fail-safe and more reasonably priced. It is particularly advantageous that with the pump device according to the invention, even extremely small leakage openings of less than a millimeter in diameter can be detected. The leak diagnosis can be advantageously achieved by the pump device according to the invention, without an air supply into the intake pipe thus preventing a disadvantageous influence on the mixture preparation.

Advantageous improvements and updates of the pump device are possible by means of the measures set forth hereafter. The pump device according to the invention distinguishes itself, moreover, by means of a particularly compact construction in which the electrical components are accommodated in a protected manner in the housing so that when water or fuel penetrates into the pump device, a failure of the pump device need not be feared. Furthermore, the high pump frequency of the pump device that is provided, in connection with a particularly precise position determination of the pump membrane by means of contact tabs provided and a contact disk attached to the pump plunger, permits a precise determination of extremely small leakage openings, wherein the operating noise of the pump device is

3 only slight. It is particularly advantageous that essential control functions of the pump device are executed automatically by means of a contact plate in the housing, outfitted with electrical components so that among other things, only a few connecting lines to an external electronic control device are required. Furthermore, the pump device according to the invention also permits the detection of larger leakage openings of the fuel vapor retention system, which can, for example, be attributed to a missing gas cap on a fuel tank of the engine.

BRIEF DESCRIPTION OF THE DRAWINGS

An exemplary embodiment of the invention is shown in simplified fashion in the drawings and explained in detail in the description below.

DESCRIPTION OF THE EXEMPLARY EMBODIMENT

Figure 1:
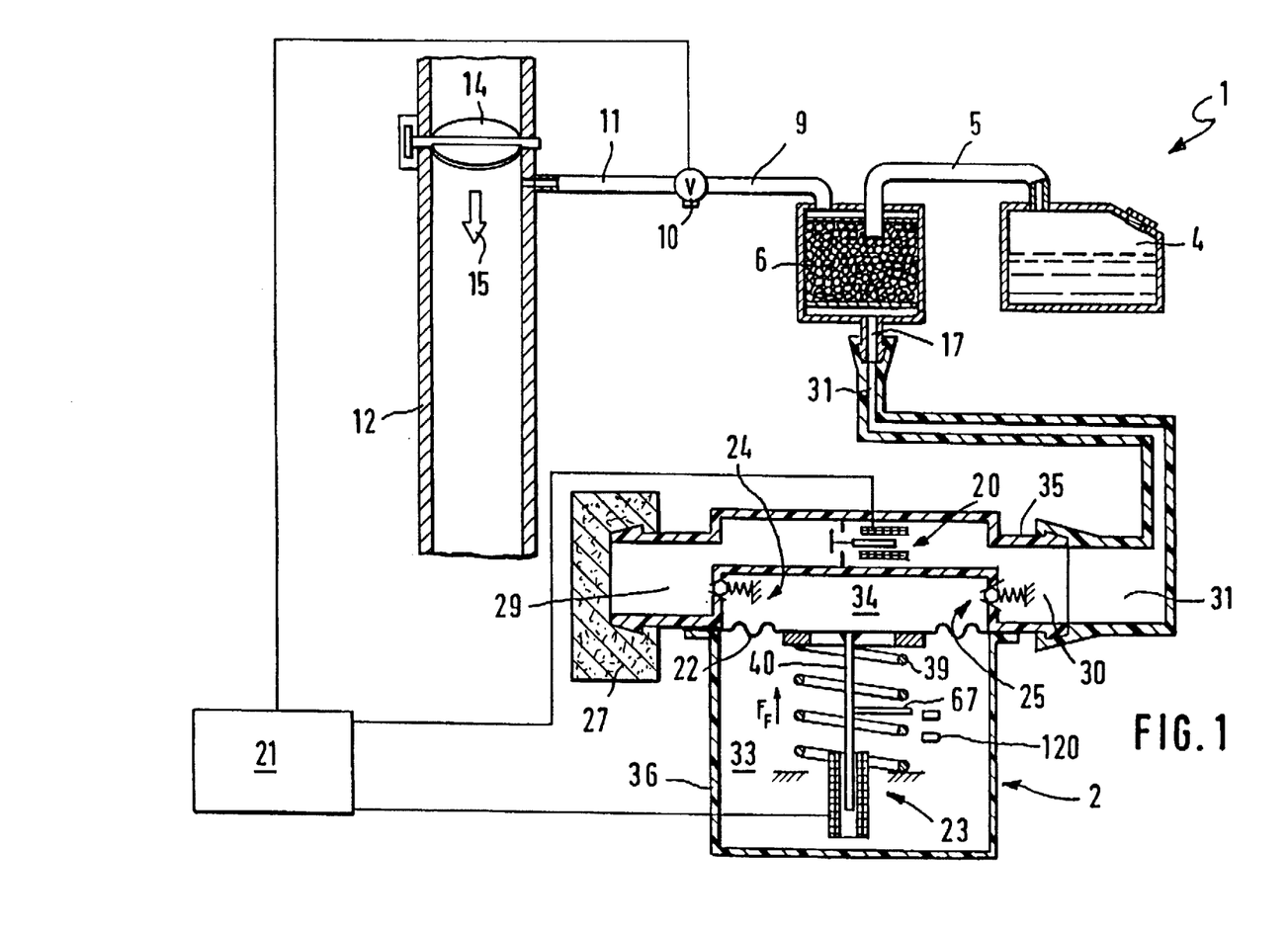
FIG. 1 shows a fuel vapor retention system for an internal combustion engine, which system has a pump device according to the invention that is depicted in a schematically simplified fashion.

FIG. 1 shows a fuel vapor retention system, which is identified with 1, which is for an internal combustion engine not shown in detail, and is equipped with a pump device 2 according to the invention depicted in a schematically simplified fashion, which produces an excess pressure for diagnostic purposes in the fuel vapor retention system 1. The fuel vapor retention system 1 also includes a fuel tank 4 for supplying the engine with fuel and an adsorption filter 6 connected to the fuel tank 4 via a tank line 5. The adsorption filter 6 is filled with an adsorption medium, in particular with activated charcoal, and connected via a connecting line 9 to a regenerating valve 10 that is connected to an intake pipe 12 of the engine via a valve line 11. The valve line 11 is connected downstream of a throttle valve 14 that is rotatably inserted into the intake pipe 12 of the engine, in which an air or fuel-air mixture flows in the direction of an arrow 15 in the drawing. During operation of the engine, a vacuum prevails in the intake pipe 12, with whose aid the fuel vapors are aspirated from the fuel tank 4 when the regenerating valve 10 is open. The fuel vapors travel from the fuel tank 4 via the tank line 5 into the adsorption filter 6 and from the adsorption filter into the connecting line 9, wherein ambient air is aspirated by means of the vacuum in the intake pipe 12 via a ventilation connection 17 provided on the adsorption filter 6 so that the fuel temporarily stored in the adsorption filter 6 is entrained in the air. The fuel vapors temporarily stored in the adsorption filter 6 mix with the ambient air flowing in via the ventilation connection 17. Via the regenerating valve 10, which is embodied for example so that it can be electromagnetically actuated and is cyclically controlled by an electronic control device 21, the fuel vapors travel via the regenerating valve 10 and the valve line 11 into the intake pipe 12 in order to then be combusted in at least one combustion chamber of the engine.

4

The regenerating valve 10 is closed for leak testing the fuel vapor retention system 1. Then, a definite volume of air is supplied to the fuel tank 4 by means of the pump device 2 via the adsorption filter 6 in order to produce a pressure increase. After the pressure increase finishes, some time is allowed to pass until the pressure has decreased again, possibly due to a leak in the fuel vapor retention system 1, wherein the time elapsed for the pressure decrease is a measure for the size of the leakage opening in the fuel vapor retention system 1. This leak testing of the fuel vapor retention system 1, also known as the excess pressure method, permits leakage openings to be detected on an order of magnitude of less than one millimeter in diameter. If the excess pressure in the fuel vapor retention system 1 does not reach the pump membrane 22 even after a particular number of pump strokes, then a large leak or a missing gas cap on the fuel tank 4 can be indicated. In the event of this, it is possible for the electronic control device 21 connected to the pump device 2 to trigger an indicator device, for example on the inside of the vehicle, to inform the driver in this manner about the malfunction occurring in the fuel vapor retention system 1.

The excess pressure required for testing purposes is supplied by the pump device 2 according to the invention, which aspirates ambient air into a delivery line 29 in the pumping process, for example via an ambient air filter 27 disposed in or on a housing 36 of the pump device 2, in order to then pump this air at increased pressure into a feed pipe 30. The feed pipe 30 is connected to the ventilation connection 17 of the adsorption filter 6, for example via a separate line 31. The pump device 2 is composed of a number of individual components that are functionally separate from one another, which are accommodated in the housing 36 and essentially comprise a pump part 23 and a stop valve 20 that can be electromagnetically actuated. The pump part 23 is provided for compressing ambient air and is composed of a pump membrane 22, a pump plunger 40, a device 67, 120 that detects the position of the pump plunger 40, a pump spring 39, and a valve device constituted by a suction relief valve 24 and a pressure relief valve 25. The pump membrane 22 divides the pump part 23 into a pump chamber 33 shown beneath the pump membrane 22 in FIG. 1 and a supply chamber 34 shown above the pump membrane 22. The supply chamber 34 is sealingly closed off from the environment by the pump membrane 22, the suction relief valve 24, and the pressure relief valve 25.

During the operation of the pump device 2, the stop valve 20 connected in parallel to the valves 24, 25, between the delivery line 29 and the feed pipe 30 assumes a closed position in order to interrupt a flow connection of the delivery line 29 to the feed pipe 30. If an operation of the pump device 2 or a leak test of the fuel vapor retention system 1 is not desired, then the stop valve 20 remains in the open position shown in FIG. 1. In the open position of the stop valve 20, when the regenerating valve 10 is open for regenerating the adsorption filter 6, ambient air can flow via the ambient air filter 27 provided at the delivery line 29 into the feed pipe 30 and from this, can flow into the adsorption filter 6 via the line 31 and the ventilation connection 17.

Figure 2:
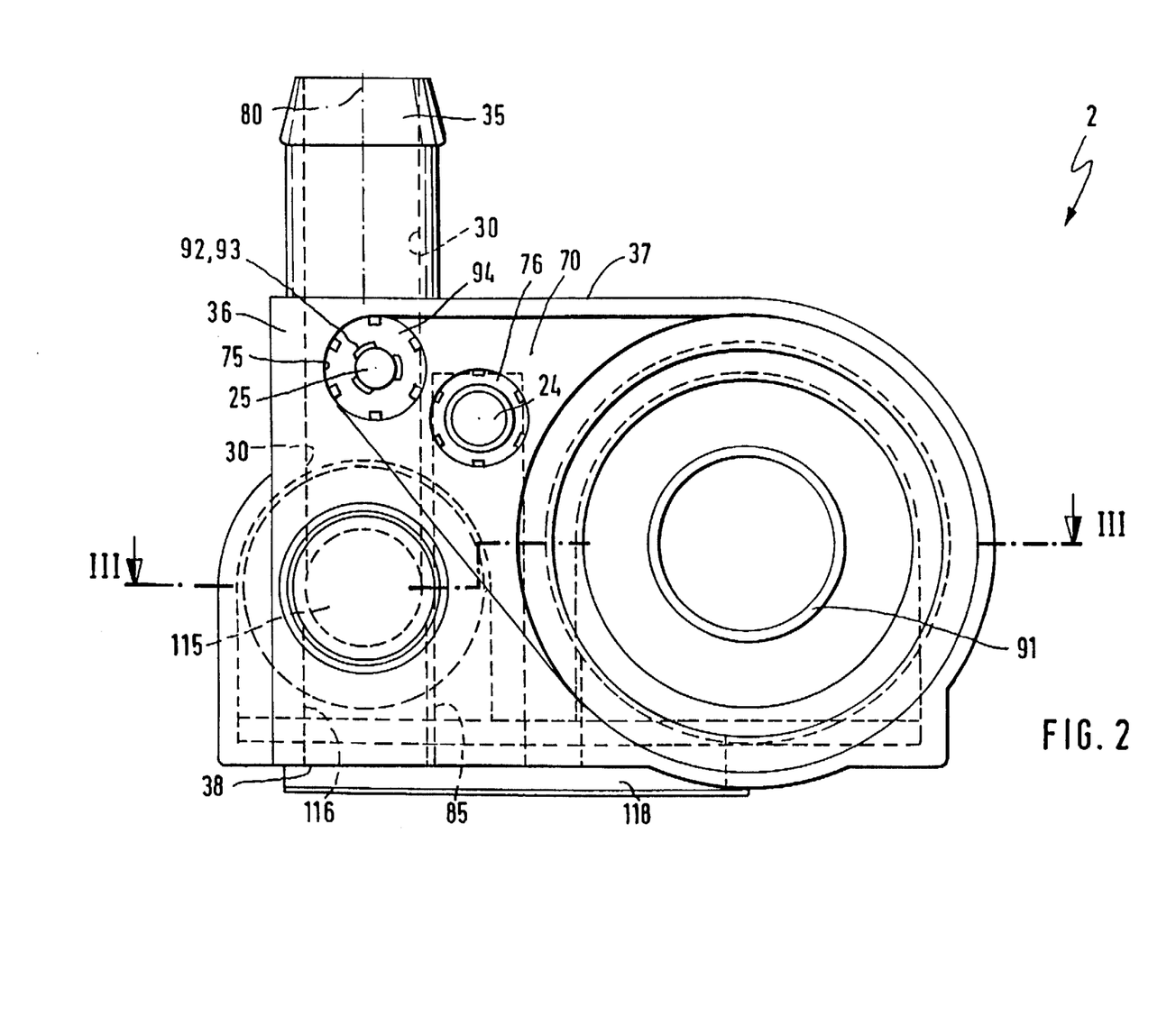
FIG. 2 shows a side view of the pump device according to the invention.

As is shown in FIG. 2, a side view of the pump device 2, the pump device 2 has a heavy, compact, one-piece, box-shaped housing 36 that is embodied essentially as a block, with a neck-shaped connection 35 that protrudes from an upper limiting face 37. The connection 35 connects with the feed pipe 30 shown in FIG. 1 and is used to connect the pump device 2 to the ventilation connection 17 of the adsorption filter 6, for example via a line 31 slid onto the connection 35 or directly, without a line 31. The housing 36 of the pump device 2 is made of plastic, for example using plastic injection molding technology, and has the required openings, raised areas, and hollowed places.

Figure 3:
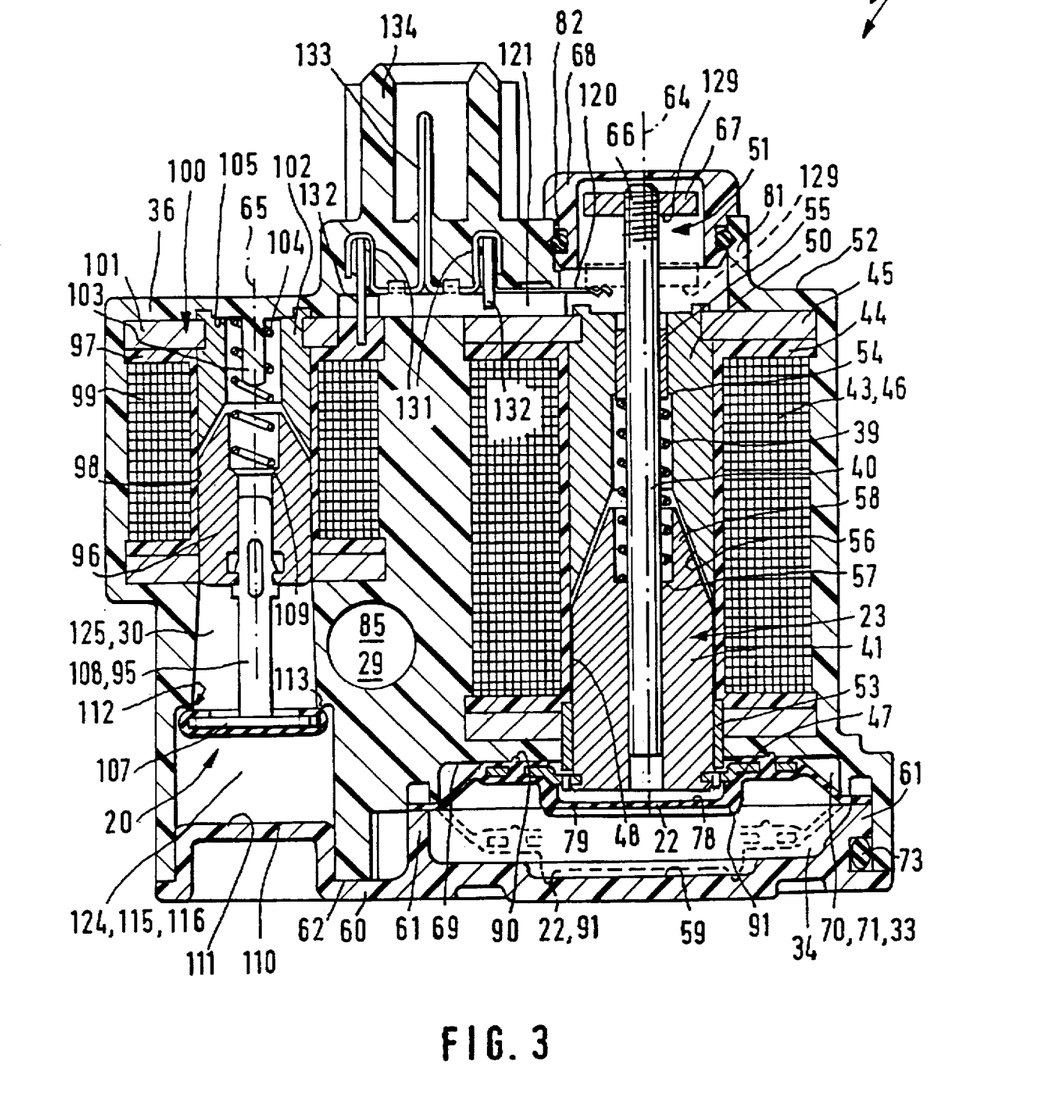
FIG. 3 shows a section along a line III—III in FIG. 2.

As is shown in FIG. 3, a section along a line III—III in FIG. 2, the pump part 23 and the stop valve 20 are accommodated in the housing 36. According to the invention, the pump part 23 is embodied in such a way that this drives the pump membrane 22 in the form of an electromagnetic drive mechanism, wherein the stop valve 20 is also embodied so that it can be electromagnetically actuated. To this end, the pump part 23 has a magnetic armature 41 attached to the pump plunger 40, which armature can be moved by magnetic forces of an electromagnet 46 that is provided in a cylindrical coil housing 44 and constituted by a trip coil 43, in order to thus electromagnetically drive the pump membrane 22, preferably with a relatively high pump frequency. The coil housing 44 is preferably comprised of plastic. The trip coil 43 is accommodated lying in the cylindrical coil housing 44 and is fastened along with the coil housing 44 to a bracket-shaped magnet housing carrier 45. The pump membrane 22 is connected to the armature 41 for example via a disk piece 47. The disk piece 47 is provided to give the pump membrane 22 a certain rigidity. The pump membrane 22 is manufactured, for example, as an injection-molded part made of plastic and is additionally reinforced, for example, by means of fluosilicone cloth.

The pump plunger 40, along with its armature 41, is accommodated so that the pump plunger can move longitudinally in a cylindrical through opening 48 that is provided in the coil housing 44, is encompassed by the trip coil 42, and extends along a longitudinal axis 64 of the pump plunger 40. A first support sleeve 53, which is attached to the coil housing 44 and the magnet housing carrier 45 in such a way that it is fixed to the housing, is provided for supporting the armature 41. Moreover a core 50, which is accommodated in the through opening 48 in the coil housing 44 and in which a second support sleeve 55 is accommodated, is provided to support the pump plunger 40 connected to the armature 41. With a contact end 51, the pump plunger 40 protrudes out from the magnet housing carrier 45 via a side face 52 of the housing 36 and is encompassed by a sleeve-shaped formation 81 of the housing 36. On its contact end 51, the pump plunger 40 has a device that detects the position of the pump plunger 40, which device is for example constituted by contact tabs 120 and a contact disk 67 that can be screwed onto an external thread 66 on the contact end 51, which tabs can be electrically connected by the contact disk 67. A closing cover 68 that can be inserted into the sleeve-shaped formation 81 seals off the contact end 51 of the pump plunger 40, which is disposed in the formation 81, from the environment, for example via a sealing ring 82.

The core 50 accommodated in the coil housing 44 has a stop recess 56 that enlarges conically toward the pump membrane 22; the armature 41 can dip partway into this stop recess. To this end, an end region of the armature 41 remote from the pump membrane 22 has an end 58 that is embodied extending conically toward the pump plunger 40 in order to be able to rest against the correspondingly conical inner surface of the stop recess 56 of the core 50. The pump spring 39 is provided around the pump plunger 40 and is accommodated inside the armature 41 and the core 50. The pump spring 39 is supported on one end against a core stop 54, which is provided inside the core 50 and formed by the second support sleeve 55, and is supported on the other end against a stop shoulder 57 provided inside the armature 41. In the currentless state of the trip coil 43, the pump membrane 22 is pressed by the spring force of the pump spring 39 against an inner wall 59 of a housing cover 60 of the housing 36 of the pump device 2 and assumes the position shown with dashed lines in FIG. 3. When the trip coil 43 is supplied with current, the pump membrane 22 rests against an inner surface 69 of a pump recess 70 that defines the pump membrane 22 and assumes the position shown with solid lines in FIG. 3.

The embodiment of the armature 41 and the core 50 as well as the dimensioning of the pump spring 39 is such that when the pump membrane 22 rests against the inner surface 69 of the pump recess 70, there is always a slight axial spacing of the armature 41 from the conical inner surfaces of the stop recess 56 of the core 50 in order, to as large an extent as possible, to prevent the armature 41 from resting against the inner surfaces of the stop recess 56 during operation, which reduces the operating noise of the pump device 2. The pump membrane 22 is disk-shaped and has at least one concentric contact bead 90 running around the longitudinal axis 64 on an end face 78 oriented toward the inner surface 69 of the pump recess 70 and has a contact bead 91 respectively on an end face 79 oriented toward the housing cover 60. When the pump membrane 22 rests against the inner surface 69 of the pump recess 70 or against the inner wall 59 of the housing cover 60, the contact bead 90 or the contact bead 91 deforms elastically, by means of which it is possible to further reduce the operation noise of the pump device 2.

Figure 4:
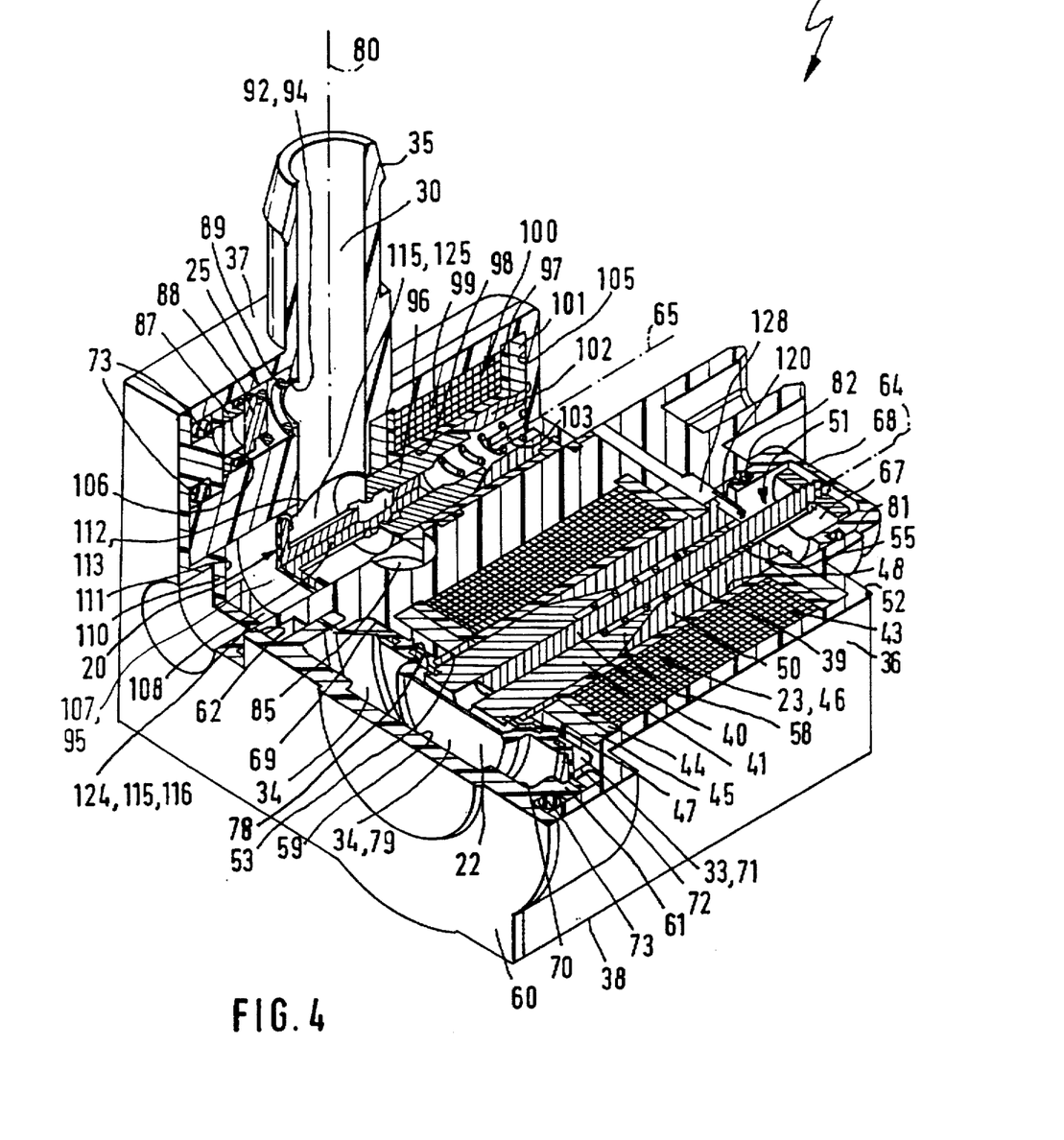
FIG. 4 shows a partial cutaway view of the pump device according to the invention in a perspective representation.
Figure 5:
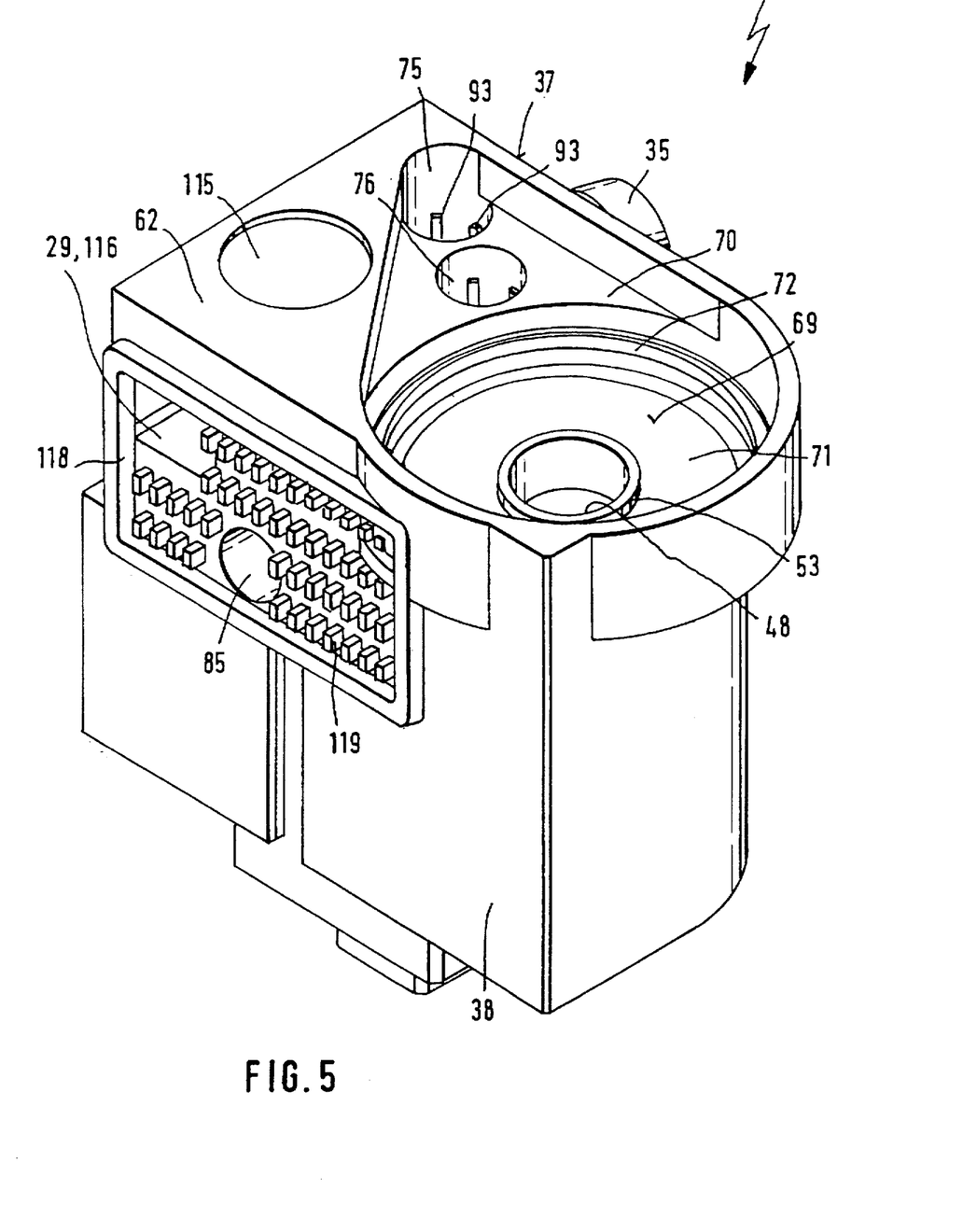
FIG. 5 shows a perspective rear view of the pump device according to the invention.

As is shown in FIG. 5, a perspective rear view of the pump device 2 without the pump membrane 22 and without the housing cover 60, the pump recess 70 has a teardrop-shaped outer contour which encloses the pump membrane 22 and valve openings 75, 76 of the valves 24, 25. The pump recess 70 is hollowed out from an end face 62 of the housing and in the provided region of the pump membrane 22, is recessed toward the coil housing 44 until the inner surface 69, and is embodied as the region encompassing the valve openings 75, 76 in order to contain the pump membrane 22 in a for example cylindrical partial recess 71 that corresponds to the shape of the pump membrane 22. The partial recess 71 is defined via a circular edge 72 of the pump recess 70 in order to clamp the pump membrane 22, which extends slightly beyond the edge 72, between the edge 72 and a strut 61 that protrudes from the inner wall 59 on the housing cover 60 and partially engages with the edge 72. The strut 61 is shown in FIGS. 3 and 4, which show the pump device 2 in a partially cutaway view. The housing cover 60 that is preferably made of plastic covers the end face 62 of the housing 36 and is held in the partial recess 71, for example, by means of clamping or detent engagement of the strut 61. However, it is also possible to fasten the housing cover 60 in another manner, for example by gluing it to the end face 62, by ultrasonic welding to the housing 36, or the like. A sealing ring 73 on the housing cover 60, which is embodied for example in the form of an O-ring, sealingly closes off the pump recess 70 from the environment. The pump membrane 22 accommodated in the partial recess 71 divides the space enclosed between the partial recess 71 and the housing cover 60 into two chambers 33, 34 that are divided from each other in a pressure tight manner, wherein the chamber 33 represents the pump chamber 33 and the chamber 34 represents the supply chamber 34 in FIG. 1. The pump chamber 33 is closed off by the pump membrane 22 and the inner surface 69 of the pump recess 70. The supply chamber 34 is closed off by the pump membrane 22, the wall of the pump recess 70, and the inner wall 59 of the housing cover 60 and extends to the valves 24, 25.

The supply chamber 34 is connected via the pressure relief valve 25, shown on the left in FIG. 2, to the feed pipe 30 which extends in the housing 36, along a longitudinal fitting axis 80 of the connection 35 drawn in FIG. 4 perpendicular to the longitudinal axis 64. The pump chamber 33 communicates with the environment or with ambient pressure via a ventilation connection, not shown in detail, provided in the housing 36. The suction relief valve 24 communicates with the environment via an intake conduit 85 provided in the housing 36, parallel to and offset from the longitudinal fitting axis 80. The intake conduit 85 extends from the upper limiting face 37 to a lower limiting face 38 of the housing 36 disposed opposite the upper limiting face 37.

The pressure relief valve 25 shown in FIG. 4 is essentially composed of a valve sleeve 87 that is inserted into the valve opening 75 and is embodied as stepped, a disk-shaped valve closing body 88 comprised of an elastic material, a valve spring 89, and a valve spring receptacle 92. The valve spring receptacle 92 is, for example, constituted by pins 93 that can be seen in FIGS. 2 and 5, that protrude into the valve opening 75 and form an annular shoulder 94 in the feed region between the valve opening 75 and the feed pipe 30, against which shoulder the valve spring 89 provided around the pins 93 can be supported on its one end. On its other end, the valve spring 89 is supported against the disk-shaped valve closing body 88, which is pressed by the spring force of the valve spring 89 against an annular sealing seat 106 of the valve sleeve 87 in order to seal the valve opening 75 so that a flow connection from the supply chamber 34 to the feed pipe 30 is interrupted. Only after there is excess pressure in the supply chamber 34, which pressure is a function of the dimensioning of the valve spring 89, does the valve closing body 88 lift off from the sealing seat 106 on the valve housing 87 in order to release the air, which is in the supply chamber 34 and is compressed by the pump membrane 22, into the feed pipe 30 via the valve opening 75 opened by the pressure relief valve 25 when the suction relief valve 24 is closed. The design of the suction relief valve 24 is carried out in a manner that corresponds to that of the pressure relief valve 25, with the difference that the valve closing body has a valve closing direction that is reversed in comparison to the pressure relief valve 25, in order to lift up from its sealing seat when there is a particular vacuum in the supply chamber 34, which vacuum is a function of the dimensioning of the valve spring, so that air can be aspirated from the intake conduit 85 into the supply chamber 34 via the valve opening 76 opened by the suction relief valve 24.

Furthermore, the stop valve 20 is accommodated inside the housing 36 of the pump device 2 as shown in FIGS. 3 and 4. The stop valve 20 has a valve closing member 95 that is disposed in the housing 36 laterally offset to the pump part 23, with a valve axis 65 running approximately parallel to the longitudinal axis 64 of the pump plunger 40 so that there are two movement axes 64, 65 that are independent of each other. The stop valve 20 is embodied according to the invention so that it can be electromagnetically actuated and to this end, has a magnetic armature 96 which is attached to the valve closing member 95 and can be moved by magnetic forces of an electromagnet 100 that is provided in a cylindrical coil housing 97 of the stop valve 20 and is constituted by a trip coil 99. The trip coil 99 is accommodated lying in the cylindrical coil housing 97 and fastened along with the coil housing 97 to a bracket-shaped magnet housing carrier 101. The coil housing 97 is preferably comprised of plastic. The armature 96 is accommodated in a cylindrical opening 98 that is provided in the coil housing 97, is encompassed by the trip coil 99, and extends along the valve axis 65 of the stop valve 20. A sleeve-shaped magnet core 102 is inserted into the opening 98 and is fastened to the magnet housing carrier 101 of the stop valve 20 in such a way that it is fixed to the housing. From an inner wall 105 in the housing 36, a pin 103 protrudes into the sleeve-shaped magnet core 102; a spring 104 is disposed around this pin and is supported on one end against the inner wall 105 of the housing 36 and on the other end against a stop 109 provided on the inside of the armature 96. The magnet housing carrier 101 of the stop valve 20 and the magnet housing carrier 45 of the pump part 23 are embodied for example as being of one piece and being embedded in the plastic of the housing 36.

The valve closing member 95 of the stop valve 20 is formed by a disk-shaped part 107, which is formed onto a plunger 108, for example of one piece with it. The plunger 108 is fastened for example on the inside of the magnetic armature 96. As shown in FIG. 3, the disk-shaped part 107 is also covered by an elastic material, for example silicone, and is accommodated in a lateral conduit 115 so that it can slide longitudinally along the valve axis 65. The lateral conduit 115 extends inside the housing 36 from the end face 62 in the direction of the valve axis 65 toward the coil housing 97 of the stop valve 20. The lateral conduit 115 is composed of a part 124 with a cylindrical cross section and a part 125 with a cross section that extends conically toward the coil housing 97. The disk-shaped part 107 of the valve closing member 95 is accommodated in the cylindrical part 124 of the lateral conduit 115, and is guided in it so that it can move longitudinally along the valve axis 65. As shown in FIGS. 2 and 4, a flow conduit 116, which for example has a rectangular cross section, flows into the cylindrical part 124 of the lateral conduit 115. The flow conduit 116 extends inside the housing 36 from the cylindrical part 124 of the lateral conduit 115, parallel to and offset from the intake conduit 85 and the longitudinal fitting axis 80 of the neck-shaped connection 35, and ends at the lower limiting face 38 of the housing 36. The conical part 125 of the lateral conduit 115 turns into the feed pipe 30 in the direction of the longitudinal fitting axis 80, which feed pipe 30 extends along the longitudinal fitting axis 80 from the conical part 125 of the lateral conduit 115 to the connection 35.

In the currentless state of the electromagnet 100 of the stop valve 20, the disk-shaped part 107 is pressed by the spring force of the spring 104 against an indentation 110 on the housing cover 60, which indentation extends slightly into the lateral conduit 115, and rests against an inner wall 111 of the indentation 110. In the currentless state, the stop valve 20 is open so that ambient air can flow via the flow conduit 116 into the cylindrical part 124 to the conical part 125 of the lateral conduit 115 and from this via the feed pipe 30 into the adsorption filter 6. In the state of the electromagnet 100 in which current is supplied, which is shown in FIG. 3, the stop valve 20 assumes a closed position. When the electromagnet 100 is supplied with current, the disk-shaped part 107 is moved away from the inner wall 111 of the indentation 110 toward the coil housing 97 in order to seal off the cylindrical part 124 of the lateral conduit 115 from the conical part 125 of the lateral conduit 115 by resting against a valve seat 112 so that a flow connection from the lateral conduit 115 to the feed pipe 30 is interrupted. The cylindrical part 124 of the lateral conduit 115 is embodied as having a slightly larger cross section than the conical part 125 of the lateral conduit 115 so that a valve seat face 113 is produced that runs around in an annular shape, against which the valve closing member 95 can sealingly rest with its disk-shaped part 107, for example with an elastic covering. Because of the partially conical embodiment 125 of the lateral conduit 115, the advantage arises that water or fuel that penetrates from the adsorption filter 6 into the feed pipe 30 via the connection 35 cannot get into the region of the electromagnet 100 of the stop valve 20, but flows out from the housing 36 under the influence of gravity because of the conical embodiment 125 of the lateral conduit 115.

As shown in FIGS. 2 and 5, the flow conduit 116 and the intake conduit 85 feed into a filter formation 118 provided on the lower limiting face 38 on the housing 36. The filter formation 118 that rises up from the lower limiting face 38 has a rectangular form, for example, and encloses a number of nubs 119 that protrude from the lower limiting face 38. The nubs 119 are provided to accommodate the ambient air filter 27 with spacing from the lower limiting face 38, between the nubs 119 and a filter cover, not shown in detail, that can be placed on the filter formation 118. The for example rectangular ambient air filter 27, not shown in detail in FIG. 5, is used to purify the ambient air aspirated by the pump device 2, which flows into the supply chamber 34 via the rectangular flow conduit 116 to the stop valve 20 and via the intake conduit 85 to the suction relief valve 24.

The operation of the pump device 2 is described below. At the beginning of the diagnosis, the regenerating valve 10 closes and the stop valve 20 is supplied with current in order to interrupt a flow connection of the feed pipe 30 to the environment in the closed position. Subsequently to or at the same time as the supplying of current to the stop valve 20, the trip coil 43 of the pump part 23 is alternatingly excited by electric current, preferably with a relatively high frequency, and de-energized again so that the pump membrane 22 moves back and forth in the pump recess 70. When the trip coil 43 of the pump part 23 is supplied with current, the magnetic armature 41 of the pump part 23 is attracted and moves with the pump membrane 22 counter to the spring force of the pump spring 39 toward the coil housing 44, by means of which a vacuum is set in the supply chamber 34 when the valves 24, 25 are closed. At a particular vacuum, the suction relief valve 24 opens in order to aspirate air from the environment into the supply chamber 34 via the intake conduit 85. In the subsequent, currentless state of the trip coil 43, the pump membrane 22 moves in the opposite direction toward the housing cover 60 due to the spring force of the pump spring 39, wherein the suction relief valve 24 closes again. When the pump membrane 22 moves toward the housing cover 60, the air enclosed in the supply chamber 34 is compressed until an opening excess pressure is reached that can be predetermined by the embodiment of the pressure relief valve 25. When the opening excess pressure in the supply chamber 34 is reached, the pressure relief valve 25 opens in order to release the compressed air in the supply chamber 34 into the adsorption filter 6 via the feed pipe 30. The pumping process by means of the pump membrane 22 is only provided for a short while until after a particular number of pump movements of the pump membrane 22, a particular excess pressure has built up in the fuel vapor retention system 1, whereupon the electromagnetic drive mechanism or the pump part 23 of the pump membrane 22 is switched off. This is occurs when the spring force of the pump spring 39 is no longer sufficient to move the pump membrane 22 downward counter to the compression force of the excess pressure in the supply chamber 34 and thus to close the contact tabs 120 by means of the contact disk 67. As a result, in comparison to a leak diagnosis by means of vacuum, the advantage arises that an otherwise conventional pressure sensor in the fuel vapor retention system 1 can be eliminated.

If there is no leakage in the fuel vapor retention system 1, then the pump membrane 22 remains pressed against the inner surface 69 of the pump recess 70 counter to the spring force of the pump spring 39 because of the excess pressure prevailing then in the supply chamber 34 as well when the pressure relief valve 25 is open. However, if there is a leak in the fuel vapor retention system 1, then the excess pressure decreases and the pump membrane 22, supported by the spring force of the pump spring 39, moves toward the housing cover 60, wherein the contact disk 67 on the pump plunger 40 assumes a position shown in FIG. 3 with dashed lines.

In the position of the contact disk 67 shown with dashed lines, for example two electrical contact tabs 120 are electrically connected to each other, with the aid of which a renewed pumping process can be triggered until a particular excess pressure has built up again in the fuel vapor retention system 1. The time required between the for example multiple actuation of the pump device 2 and the reinstatement of the excess pressure is a measure for the size of the leakage opening that has occurred. However, if no excess pressure is adjusted even after multiple pumping processes, then this can be attributed to a particularly large leakage opening or to a missing gas cap on the fuel tank 4.

Figure 6:
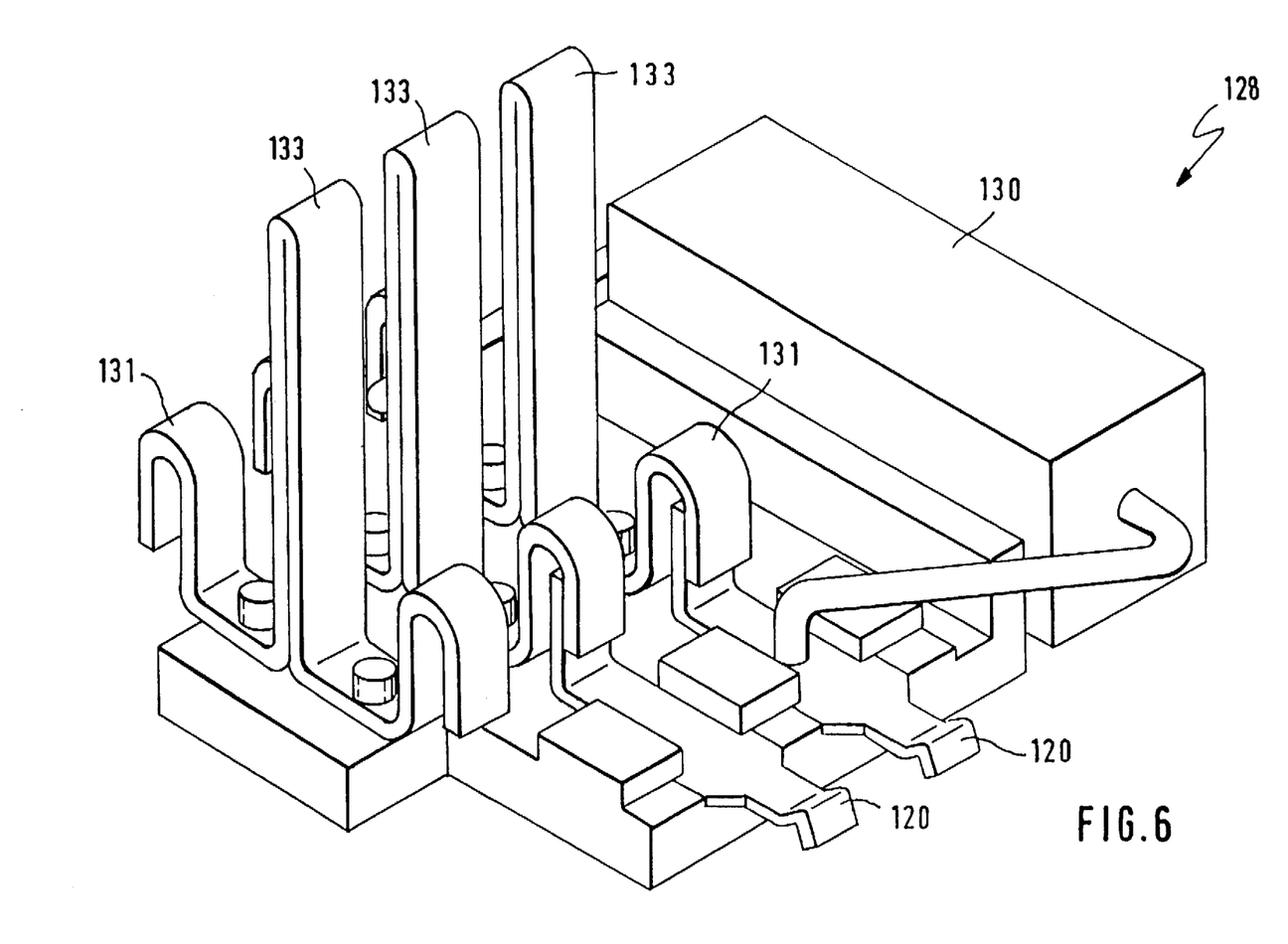
FIG. 6 shows a perspective view of a component of the pump device according to the invention.

The contact tabs 120 are accommodated in the housing 36, on a contact plate 128 represented in perspective in FIG. 6, in the region of the contact end 51 of the pump plunger 40. As shown in FIGS. 3 and 4, the two contact tabs 120 protrude outside the coil housing 44 of the pump part 23 into the chamber defined by the formation 81 and the closing cover 68 used. In the position of the contact disk 67 shown with dashed lines in FIG. 3, both contact tabs 120 are connected to each other at a contact surface 129 of the contact disk 67, which surface is oriented toward the coil housing 44 so that an electrical connection is produced. To this end, the contact disk 67 has a finely machined contact surface 129 in order to permit a great number of electrical contacts, in particular without sparking. Furthermore, as shown in FIG. 6, the contact plate 128 has a number of electrical components 130 that are provided, for example, in the form of electrical resistors for triggering the pump part 23 and the stop valve 20. To this end, the electrical components 130 of the contact plate 128 are connected via angled contact brackets 131 and are connected to the electromagnet 100 of the stop valve 20 and the electromagnet of the pump part 23 via contact pins 132 shown in FIG. 3. The contact plate 128 can furthermore be electrically contacted by an electrical plug that can be coupled to the plug receptacle 134 via plug tabs 133, which are engaged in a plug receptacle 134 formed on the upper limiting face 37 on the housing 36. The plug produces a connection of the pump device 2 to the electronic control device 21 that is provided, for example, externally and is provided, for example, for the cyclical triggering of the regenerating valve 10, for triggering the stop valve 20 and the pump part 23, as well as for evaluating the electrical signals emitted by the pump device 2. By means of the electrical components 130, it is possible to carry out essential control functions of the pump device 2, in particular of the pump part 23 and of the stop valve 20 automatically, that is, without the aid of the electronic control device 21 so that only a few connecting lines to the electronic control device 21 are required. However, it is also possible to accommodate a corresponding evaluation circuit in the housing 36 itself, which is embodied for example in hybrid construction and is attached for example to the contact plate 128.

The foregoing relates to preferred exemplary embodiments of the invention, it being understood that other variants and embodiments thereof are possible within the spirit and scope of the invention, the latter being defined by the appended claims.

What is claimed and desired to be secured by Letters Patent of the United States is:

1. A pump device for a fuel vapor retention system of an internal combustion engine, comprising a pump membrane that defines a supply chamber with a valve device, a first valve and a second valve by means of said first valve, the supply chamber can be connected to ambient air via a delivery line and by means of said second valve, the supply chamber can be connected to an adsorption filter via a feed pipe, a stop valve provided between the delivery line and the feed pipe, said pump membrane (22) is embodied so that the pump membrane can be moved by an electromagnetic drive mechanism (23) and the stop valve (20) is embodied so that it can be electromagnetically actuated.

2. A pump device according to claim 1, in which the pump membrane (22) with the electromagnetic drive mechanism (23) and the stop valve (20) that can be electromagnetically actuated are accommodated in a common housing (36) of the pump device (2).

3. A pump device according to claim 1, in which a pump plunger (40) is attached to the pump membrane (22) and has a first magnetic armature (41) that can be moved by a first electromagnet (46).

4. A pump device according to claim 2, in which the stop valve (20) has a valve closing member (95) to which a second magnetic armature (96) is attached that can be moved by a second electromagnet (100).

5. A pump device according to claim 4, in which the valve closing member (95) of the stop valve (20) is embodied as disk-shaped and is accommodated in a first part (124) of a lateral conduit (115) provided in the housing (36), said first part has a cylindrical cross section and transitions into a second part (125) of the lateral conduit (115) that has a conical cross section, wherein a valve seat (112) of the valve closing member (95) is embodied at a transition point of a cylindrical first part (124) to a conical second part (125).

6. A pump device according to claim 2, in which the stop valve (20) and the electromagnetic drive mechanism (23) of the pump membrane (22) have movement axes (64, 65) in the housing (36) that are independent of each other.

7. A pump device according to claim 2, in which the delivery line (29) is constituted by first and second separate conduits (85, 116) provided in the housing (36).

8. A pump device according to claim 2, in which the pump membrane (22) is disposed in a recess (70, 71) provided on an end face (62) of the housing (36) and can be sealingly closed by a housing cover (60) that can be placed on an end face (62) of the housing (36).

9. A pump device according to claim 3, in which a device (67, 120) that detects a position of the pump plunger (40) is provided on an end (51) of the pump plunger (40) disposed opposite from the pump membrane (22).

10. A pump device according to claim 9, in which the position detection device (67, 120) is constituted by a disk (67) attached to an end (51) of the pump plunger (40) and includes at least two electrical contacts (120) that can be electrically connected to each other by the disk (67).

11. A pump device according to claim 2, in which means (128, 130) are provided in the housing (36) or on the housing (36) and are for triggering the electrical drive mechanism (23) of the pump membrane (22) and triggering the stop valve (20) that can be electromagnetically actuated.

12. A pump device according to claim 10, in which electrical components (130) of a contact plate (128) are electrically connected to the first electromagnet (46) of the electrical drive mechanism (23) and electrically connected to the second electromagnet (100) of the stop valve (20) and permit a triggering of the first electromagnet (46) of the electrical drive mechanism (23) and a triggering of the second electromagnet (100), of the stop valve (20) via the contact tabs (120) by means of the disk (67).

13. A pump device according to claim 11, in which electrical components (130) of a contact plate (128) are electrically connected to the first electromagnet (46) of the electrical drive mechanism (23) and electrically connected to the second electromagnet (100) of the stop valve (20) and permit a triggering of the first electromagnet (46) of the electrical drive mechanism (23) and a triggering of the second electromagnet (100) of the stop valve (20) via the contact tabs (120) by means of the disk (67).

14. A pump device according to claim 1, in which a filter (27) is provided to purify the ambient air aspirated by the pump device (2).

* * * * *